United States Patent [19]

Krebber

[11] Patent Number: 4,704,141
[45] Date of Patent: Nov. 3, 1987

[54] APPARATUS FOR AUTOMATICALLY TRANSFERRING SMALL QUANTITIES OF LIQUID SAMPLES IN GAS CHROMATOGRAPHY

[75] Inventor: Ernst-Werner Krebber, Keltern-Weiler, Fed. Rep. of Germany

[73] Assignee: Siemens Aktiengesellschaft, Berlin and Munich, Fed. Rep. of Germany

[21] Appl. No.: 875,431

[22] Filed: Jun. 17, 1986

[30] Foreign Application Priority Data

Jun. 20, 1985 [DE] Fed. Rep. of Germany ....... 3522125

[51] Int. Cl.⁴ ............................................. B01D 15/08
[52] U.S. Cl. ........................................ 55/197; 55/386; 73/23.1; 73/864.11
[58] Field of Search ............................ 55/67, 197, 386; 73/23.1, 864.01, 864.11; 604/44, 411, 414

[56] References Cited

U.S. PATENT DOCUMENTS

| | | | |
|---|---|---|---|
| 2,409,343 | 10/1946 | Curtis | 604/411 |
| 3,324,628 | 6/1967 | Natelson | 55/67 |
| 3,365,951 | 1/1968 | Jentzsch et al. | 55/197 X |
| 3,408,793 | 11/1968 | Frazer | 55/197 |
| 3,475,964 | 11/1969 | Jenkins | 55/197 X |
| 3,540,852 | 11/1970 | Gorne et al. | 55/67 X |
| 3,608,550 | 9/1971 | Stawski | 604/414 |
| 3,626,761 | 12/1971 | Haruki et al. | 55/197 X |
| 3,887,345 | 6/1975 | Pollock et al. | 55/386 |
| 3,920,420 | 11/1975 | Valentine et al. | 55/67 |
| 4,224,943 | 9/1980 | Johnson et al. | 604/44 X |
| 4,405,344 | 9/1983 | Sisti et al. | 55/67 |
| 4,464,940 | 8/1984 | Pospisil | 73/864.21 |
| 4,474,588 | 10/1984 | Hinshaw, Jr. | 55/386 X |
| 4,476,734 | 10/1984 | Banks et al. | 73/864.16 |
| 4,540,402 | 9/1985 | Aigner | 604/44 |

FOREIGN PATENT DOCUMENTS 1673028 11/1972 Fed. Rep. of Germany .
1179459 1/1970 United Kingdom .

Primary Examiner—Robert Spitzer
Attorney, Agent, or Firm—Lawrence C. Edelman

[57] ABSTRACT

A gas chromatograph, very small sample metering apparatus having a double hollow needle that is inserted downward into the sample vial to transfer pneumatically the entire sample quantity, on the order of 1 microliter, from the sample vial, through a transfer capillary with an inside diameter of between 0.1 and 0.15 mm, directly to the cold, temperature-programmable vaporizer. The sample is retained in the vaporizer for later vaporization. While the sample is being vaporized and injected into the gas-chromatographic separation column, the transfer capillary line is backwashed with a flushing solvent which is transferred by a carrier gas through the interconnecting tubular lines.

7 Claims, 3 Drawing Figures

APPARATUS FOR AUTOMATICALLY TRANSFERRING SMALL QUANTITIES OF LIQUID SAMPLES IN GAS CHROMATOGRAPHY

FIELD OF THE INVENTION

This invention relates to the field of chromatography and more particularly to an apparatus for automatically transferring small quantities of liquid samples from sample vials into the temperature-programmed vaporizer of a gas-chromatographic analytical instrument.

BACKGROUND OF THE INVENTION

Known metering devices require between 20 and 100 microliters of sample liquid in order that a volumetrically determined sample quantity of 1 microliter can be metered into the injector. Unfortunately, sample quantities of this order of magnitude are often not available, for example when physiological fluids, which occur in quantities of 1 to 2 microliters, are under investigation. Accordingly, there is the problem of metering a quantity sufficient for analysis even when the sample quantities are very small, on the order of 1 microliter. Because of small sample sizes dead or unused volumes in the transfer line between the sample vessel and the injector are to be avoided.

SUMMARY OF THE INVENTION

It is an object of this invention to provide an apparatus for transferring all of a very small sample from a sample vial to a gas chromatographic separation column. It is a further object of this invention to provide a self flushing transferring apparatus so subsequent very small samples are not contaminated with residues of previous samples.

Briefly stated in accordance with one aspect of the invention these objects are achieved by providing an apparatus for automatically transferring a small quantity of a liquid sample from a sample vial to a temperature-programmed vaporizer of a gas chromatographic analytical instrument. This apparatus includes: a septum sealing the sample vial such that only the small quantity of the liquid to be metered is contained therein; a hollow needle for supplying a carrier gas and for withdrawing the small quantity of the liquid sample, which is inserted through the septum and rests with one end against a bottom of the sample vial; a transfer capillary for transporting the withdrawn liquid sample, connected at one end to a first junction of a tee connection; a second junction of the tee connection is connected to the temperature-programmable vaporizer; said liquid sample after being withdrawn from the sample vial by the hollow needle and after being transported by the transfer capillary is retained in temperature-programmed vaporizer which is initially programmed for a non-vaporizing temperature; and a flushing solvent is transported by the carrier gas through a third junction of the tee connection and the transfer capillary, after the supply of carrier gas to the sample vial has been cut off and the hollow needle has been withdrawn from the sample vial, to provide a backflushing.

With this apparatus, the whole sample can be transferred from the sample vial into the separation column; that is, even the smallest sample quantities, on the order of 1 microliter, are still meterable.

Because the transfer and injection of the sample are done pneumatically, with the help of a carrier gas, there are no valves or similar devices in the transfer line between the sample vial and the vaporizer, and said transfer line is practically free of dead or unused volume.

The volumetric measurement of the sample quantity to be metered can be dispensed with.

BRIEF DESCRIPTION OF THE DRAWINGS

While the specification concludes with claims particularly pointing out and distinctly claiming the subject matter which is regarded as the invention, it is believed that the invention will be better understood from the following description of the preferred embodiment taken in conjunction with the accompanying drawings in which:

DESCRIPTION OF A PREFERRED EMBODIMENT

Figure 1:
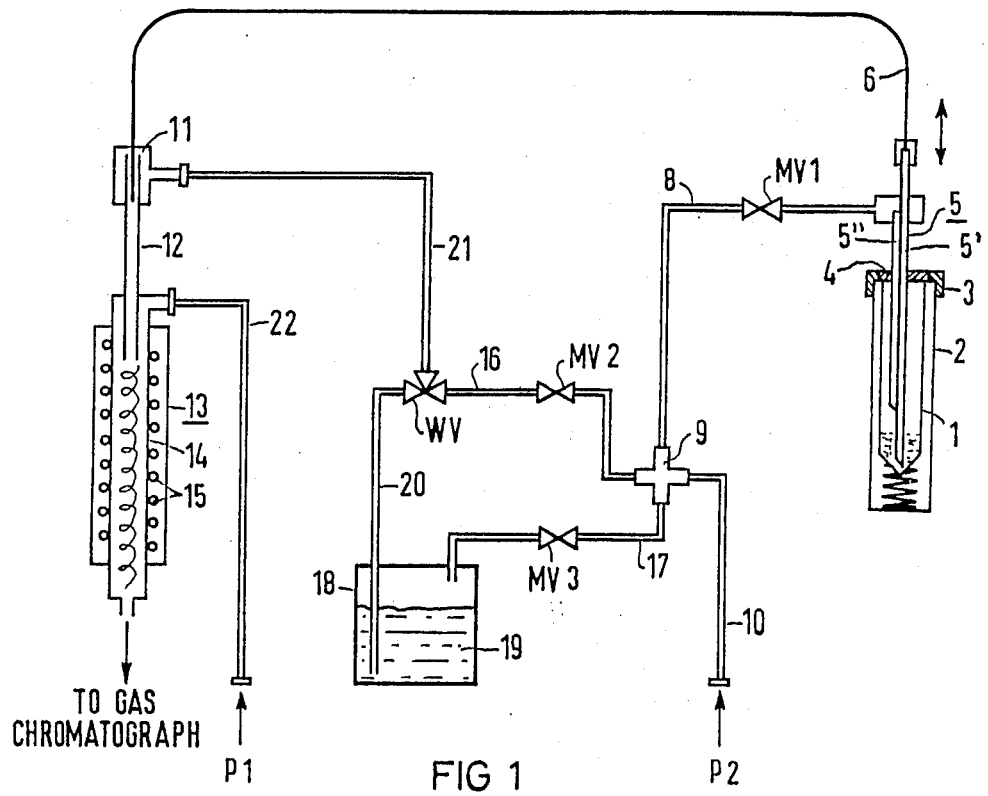
FIG. 1 shows schematically a transfer apparatus.

As shown in FIG. 1, a small quantity of sample liquid, say 1 microliter, is located in the conically tapered bottom portion of a sample vial 1, which is held by an axial spring inside a sample vessel 2 and is provided with a tightly closing lid 3.

The lid 3 has a pierceable septum 4 through which a vertically movable double hollow needle 5 can be inserted in the sample vial 1. The double hollow needle 5 consists of a longer hollow needle 5', which reaches to the bottom of the sample vial 1. The second hollow needle 5" is shorter and opens into the space above the liquid surface in the sample bottom 1. The upper end of the longer hollow needle 5' is connected to a transfer capillary, whose inside diameter is 0.1 to 0.15 mm, while the top end of the second hollow needle 5" is connected, through a pressure line 8, to the magnetically actuated valve MV1 on a distributor 9. The distributor 9 is supplied from a source of carrier gas with a constant pressure $p_2$ through the line 10.

The transfer capillary 6 opens into an intermediate capillary 12 with an inside diameter between 0.3 and 0.5 mm inside a tee 11.

This intermediate capillary 12, in turn, opens into the inner tube 14 of a temperature-programmable vaporizer 13, which is enclosed by a heating and cooling coil 15 and is connected to the gas-chromatographic separation column not shown here.

The distributor 9, supplied with carrier gas at pressure $p_2$ through the line 10, has a further line 16 issuing from it, said line 16 containing a magnetically actuated valve MV2 and said line being connected to one port of a three-way, three-position valve WV.

A further line 17 issuing from the distributor 9 leads, through a magnetically actuated valve MV3, to a container 18, which contains a flushing solvent 19, and said line 17 has its opening there above the liquid surface.

From the container 18, a line 20, which reaches to the bottom of the said container 18, leads to the second port of the three-way valve WV, whose outlet is connected through a line 21, to the third port of the tee 11.

A line 22, which is connected to a carrier-gas source at a constant pressure $p_1$, has its opening at the top end of the inside tube 14 in the temperature-programmable vaporizer 13. The pressure $p_1$ is lower than $p_2$.

The automatic metering process takes place in the following manner: Assume initially all magnetically actuated valves and the three-way valve are closed.

The sample vessel 2 with the sample vial 1 is placed in the sampling position and the double hollow needle 5 is inserted vertically downward through the septum 4 until the longer hollow needle 5' is immersed in the liquid sample located at the bottom of the conical taper of the sample vial 1. The magnetically actuated valve MV1 is opened; the carrier gas entering the sample vial 1 through the second, shorter hollow needle 5" forces the entire sample into the hollow needle 5', and from there through the transfer capillary 6 into the intermediate capillary 12.

As the magnetically actuated valve MV1 closes in line 8, the magnetically actuated valve MV2 opens into line 16, which, through the three-way valve WV and line 21, supplies carrier gas to the tee 11 and from there to the intermediate capillary 12, so that the entire sample is carried into the inside tube 14 of the vaporizer, which is initially at a cold, non-vaporizing temperature where it is retained, for example, in a glass-wool packing.

The double needle 5 is withdrawn from the sample vessel, the magnetically actuated valve MV2 is closed, and the magnetically actuated valve MV3 opened; in this fashion, carrier gas at the pressure $p_2$ is admitted to the flushing solvent container 18 through the line 17, so that the flushing solvent 19 is forced through the line 20 and the appropriately positioned three-way valve WV into the line 21, and from there into the tee 11. Because the pressure difference between $p_2$ and atmospheric pressure at the outlet of the hollow needle 5' is greater than the pressure difference between $p_2$ and $p_1$ at the inlet to the inside tube of the temperature-programmable vaporizer 13, the flushing solvent is forced by way of the transfer capillary 6 through the hollow needle 5' so that it backwashes the entire transport path. At the same time, the heating and cooling coil 15 in the temperature- programmable vaporizer 13 is turned on and the liquid sample therein is flash-evaporated and carried, by means of the carrier gas at pressure $p_1$ admitted through the line 22, into the gas -chromatography separation column. Finally the magnetically actuated valve MV3 closes, MV2 opens, and the three-way valve connects the lines 16 and 21, so that the transport path through the transfer capillary 6 and the hollow needle 5' can be blown dry. A subsequent sample vessle is placed in the intake position and the automatic sample liquid metering process is repeated.

Figure 2:
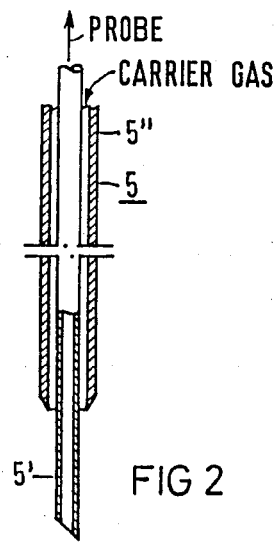
FIGS. 2 and 3 show in partial section two different embodiments of the double hollow needles used for withdrawing the sample.

In FIG. 2 an embodiment of the double hollow needle 5 is shown. It consists of two hollow needles 5' and 5", arranged coaxially one inside the other, the inner hollow needle 5' being, as already described, of such a length that it reaches to the bottom of a sample vial. The outer, shorter hollow needle 5" serves to deliver the carrier gas through the annular clearance formed between the two hollow needles 5' and 5" for the purpose of pneumatically transferring the sample.

Figure 3:
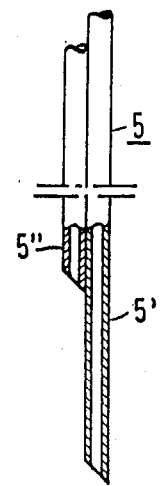

In FIG. 3 another embodiment of the double hollow needle 5 is shown. It consists of two hollow needles 5' and 5", preferably of the same diameter but of different lengths, connected parallel to each other, the hollow needle 5' serving to transfer the sample and the hollow needle 5" serving to supply the carrier gas.

It will now be understood that there has been disclosed an improved system for transferring small quantities of liquid samples into a gas-chromatograph. As will be evident from the foregoing description, certain aspects of the invention are not limited to the particular details of the examples illustrated, and it is therefore contemplated that other modifications or applications will occur to those skilled in the art. It is accordingly intended that the claims shall cover all such modifications and applications as do not depart from the true spirit and script of the invention.

I claim:

1. An apparatus for transferring a small quantity of a liquid sample from a sample vial to a temperature-programmed vaporizer of a gas-chromatographic analytical instrument, comprising:
   a septum sealed sample vial containing only the small quantity of the liquid sample to be metered:
   means for supplying a carrier gas under pressure into said sample vial and means for withdrawing the small quantity of the liquid sample, said means for supplying and means for withdrawing being inserted through the septum;
   a transfer capillary for transporting the withdrawn liquid sample connected at one end to said means for withdrawing and at the other end to a first junction of a tee connection;
   means for connecting a second junction of the tee connection to the temperature-programmed vaporizer;
   said liquid sample, after being withdrawn from the sample vial by said means for withdrawing and after being transported by the transfer capillary, is retained in the temperature-programmed vaporizer which is programmed for a non-vaporizing temperature; and
   means for transporting a flushing solvent by the carrier gas through a third junction of the tee connection and the transfer capillary after the supply of carrier gas to the sample vial has been cut off and said means for supplying and withdrawing has been withdrawn from the sample vial, to provide a back-flushing.

2. An apparatus according to claim 1, wherein the transfer capillary has an inside diameter of 0.1 to 0.15 mm.

3. An apparatus according to claim 1, wherein:
   the transfer capillary inside the tee opens into an intermediate capillary having an inside diameter between 0.3 mm and 0.5 mm, which in turn opens into the temperature programmable vaporizer; and
   the third junction of the tee is connected by a first tubular line to a three-way valve through which can be suitably supplied either pressurized carrier gas through a second tubular line connected to the three-way valve, or flushing solvent through a third tubular line, also connected to the three-way valve.

4. An apparatus for automatically transferring a small quantity of a liquid sample from a sample vial to a temperature-programmed vaporizer of a gas-chromatographic analytical instrument, comprising:
   a septum sealed sample vial containing only the small quantity of the liquid sample to be metered;
   a double hollow needle, including two hollow needles connected together, said hollow needles having two different lengths and being inserted through the septum with the longer one of said hollow needles having one end resting against the bottom of the sample vial for withdrawing the sample and the shorter one of said hollow needles ending above the liquid sample for supplying a pressurized carrier gas into the sample vial;

a transfer capillary for transporting the withdrawn liquid sample connected at one end to the longer hollow needle and at the other end to a first junction of a tee connection;

means for connecting a second junction of the tee connection to a temperature-programmed vaporizer;

said liquid sample, after being withdrawn from the sample vial by the longer hollow needle and after being transported by the transfer capillary, is retained in the temperature-programmed vaporizer which is programmed for a non-vaporizing temperature; and means for transporting a flushing solvent by the carrier gas through a third junction of the tee connection and the transfer capillary after the supply of carrier gas to the sample vial has been cut off and the double hollow needle has been withdrawn from the sample vial, to provide a backflushing.

5. An apparatus according to claim 4, wherein the double hollow needle consists of two hollow needles, of different lengths connected parallel to each other.

6. An apparatus according to claim 5, wherein said two hollow needles are of the same diameter.

7. An apparatus according to claim 4, wherein the double hollow needle consists of two hollow needles of different lengths, arranged coaxially, one inside the other.

* * * * *